United States Patent [19]

Yoshida et al.

[11] Patent Number: 4,743,449

[45] Date of Patent: May 10, 1988

[54] DRUG-CONTAINING LIPID VESICLE PREPARATION AND METHOD FOR PREPARING THEM

[75] Inventors: Hiromitsu Yoshida, Kyoto; Jiro Fujisaki, Amagasaki; Seiji Sawai, Neyagawa, all of Japan

[73] Assignee: Fujisawa Pharmaceutical Co., Ltd., Osaka, Japan

[21] Appl. No.: 648,961

[22] Filed: Sep. 10, 1984

[30] Foreign Application Priority Data

Sep. 12, 1983 [JP] Japan ................... 58-168824

[51] Int. Cl.[4] ............ A61K 39/02; A61K 39/12; A61K 39/18
[52] U.S. Cl. ..................... 424/420; 264/4.1; 514/866
[58] Field of Search ............ 424/38, 420; 264/4.1

[56] References Cited

U.S. PATENT DOCUMENTS

| | | | |
|---|---|---|---|
| 4,201,767 | 5/1980 | Fullerton et al. | 424/89 |
| 4,235,877 | 11/1980 | Fullerton | 424/89 |
| 4,261,975 | 4/1981 | Fullerton et al. | 424/89 |
| 4,356,167 | 10/1982 | Kelly | 424/38 |
| 4,452,747 | 6/1984 | Gersonde et al. | 424/38 |
| 4,508,703 | 4/1985 | Redziniak et al. | 424/38 |
| 4,515,736 | 5/1985 | Deamer | 424/38 |
| 4,532,089 | 7/1985 | MacDonald | 424/38 |
| 4,619,794 | 10/1986 | Hauser | 424/38 |

FOREIGN PATENT DOCUMENTS 102324  3/1984  European Pat. Off. .
130577  1/1985  European Pat. Off. .

*Primary Examiner*—Ronald W. Griffin
*Attorney, Agent, or Firm*—Jordan B. Bierman

[57] ABSTRACT

Drug-containing lipid vesicle preparations are prepared by adding an aqueous solution or suspension to a phospholipid which contains a lipophilic surfactant to form a mixture, stirring said mixture whereby lipid vesides are formed, then dispersing said vesicles in a dispersion medium to form an emulsion.

10 Claims, No Drawings

DRUG-CONTAINING LIPID VESICLE PREPARATION AND METHOD FOR PREPARING THEM

The present invention relates to a drug-containing lipid vesicle preparation which is a novel form of pharmaceutical preparation, and a method of preparing thereof.

Liposomes, multiple emulsions of the W/O/W type, etc. are known as preparations developed for improving the biological or physical properties of pharmaceuticals.

Although effective for sustained release and tissue localization of drugs, liposomes have the drawback that the amount of drug that can be contained therein is limited.

On the other hand, multiple emulsions have the characteristics of containing an increased amount of drug and being amenable to migration to the lymphatic system, whereas they have the drawback of being low in stability.

The present inventors have carried out intensive research to develop a preparation having the characteristics of both the liposome and the multiple emulsion and consequently accomplished the present invention.

The drug-containing lipid vesicle preparation of the present invention is a kind of novel drug carrier and is obtained by stirring and mixing an aqueous solution or an aqueous suspension together with a phospholipid containing a lipophilic surfactant at least one of which contains a drug, and dispersing the resulting lipid vesicles in a dispersion medium. When the dispersion medium is liquid, the dispersion obtained above may be further freeze-dried or spray-dried.

For the production of the preparation of this invention, an aqueous solution or an aqueous suspension, and a phospholipid containing a lipophilic surfactant are first mixed together by stirring. In this case, a drug is contained in the aqueous solution or the aqueous suspension, and/or the phospholipid containing a lipophilic surfactant. The drug is preferably water-soluble when to be incorporated into the aqueous solution or aqueous suspension. If the drug has low solubility in water, a suitable solubilizer may be used to prepare an aqueous solution, or a suitable suspending agent may be used to prepare an aqueous suspension. The drug concentration of the aqueous solution or suspension, i.e. of the inner liquid phase, is not limited particularly but can be determined suitable in view of the variation of dissolving-out time due to the osmotic pressure difference relative to the dispersion medium to be stated later. An osmotic pressure adjusting agent, such as sodium chloride or glucose, may be suitably added to the inner liquid phase in order to adjust the osmotic pressure of the liquid phase.

Examples of the lipohilic surfactants are sorbitan fatty acid esters such as sorbitan sesquioleate and sorbitan tristearate, polyoxyethylene sorbitol fatty acid esters such as polyoxyethylene (6) sorbitol hexastearate, glycerin fatty acid esters such as glyceryl monostearate, propylene glycol fatty acid esters such as propylene glycol monostearate, polyethylene glycol fatty acid esters such as polyoxyethylene (2) monostearate, etc.

Exemplary of useful phospholipids are natural phospholipids such as soybean lecithin, egg yolk lecithin, sphingomyelin, phosphatidyl serine, phosphatidyl glycerol, phosphatidyl inositol, diphosphatidyl glycerol, phosphatidylethanolamine, etc., and synthetic phospholipids such as phosphatidyl choline, distearoyl phosphatidyl choline, dipalmitoyl phosphatidyl choline, dipalmitoyl phosphatidylethanolamine, etc. Especially preferable is a mixture of phosphatidyl cholines, phosphatidylethanolamine and phosphatidyl inositol in approximately equal amounts such as soybean lecithin.

Although the content of the lipophilic surfactant in the phospholipid is not limited particularly, preferred results are usually achieved when the amount of the lipophilic surfactant is 0.1 to 1 part by weight per 1 part by weight of the phospholipid.

Such a phospholipid containing a lipophilic surfactant forms a so-called membrane portion of the lipid vesicles. To adjust the fluidity and stability of the membrane forming material or the permeability of the drug in the inner liquid phase across the membrane, cholesterols, dicetyl phosphate, phosphatidic acid, stearylamine, $\alpha$-tocopherol may be added to the membrane forming material. The membrane forming material may have further incorporated therein a vegetable oil such as sesame oil, peanut oil or the like, an animal oil such as beef tallow, liver oil or the like, a synthetic oil such as monoglyceride, triglyceride or the like, or an oily vitamin such as vitamin A, vitamin D, vitamin E or the like in an amount of about 0.05 to 0.5 part by weight per 1 part by weight of the phospholipid.

When a drug is to be contained in the membrane forming material, i.e. the phospholipid containing a lipophilic surfactant, thus prepared, the drug is preferably lipophilic. If the membrane forming material has the above-mentioned oily substance incorporated therein, an increased amount of drug can be contained in the membrane forming material.

Although the mixing proportions of the phospholipid containing a lipophilic surfactant for forming the membrane portion and the foregoing aqueous solution or suspension for forming the inner liquid phase are not limited particularly, it is usually desirable that the former to latter ratio be approximately 1:5 to 9 by weight. The two ingredients are mixed together under conditions sufficient to form an emulsion.

The lipid vesicles thus prepared are then dispersed in a dispersion medium.

Examples of the dispersion media are aqueous solution of hydrophilic surfactants, aqueous ointment bases such as polyethylene glycol, propylene glycol and carboxymethylcellulose, oily ointment bases such as vaseline, fluid paraffin and white Japan wax, organic solvents such as xylene, ethyl acetate and cyclohexane, etc.

Examples of hydrophilic surfactants for preparing aqueous solutions of such surfactants for use as dispersion media are nonionic surfactants including polyoxyethylene sorbitan fatty acid esters such as polyoxyethylene sorbitan monooleate and polyoxyethylene monolaurate, polyoxyethylene fatty acid esters such as polyoxyethylene stearate, polyoxyethylene alkyl ethers such as polyoxyethylene cetyl ether, polyoxyethylene hardened castor oil derivatives such as polyoxyethylene (60) hardened castor oil, etc.; anionic surfactants including alkylsulfuric acid ester salts such as sodium laurylsulfate; cationic surfactants including benzalkonium chloride; amphoteric surfactants; and high-molecular-weight surfactants. Also useful are proteins which behave like hydrophilic surfactants. The concentration of such a hydrophilic surfactant in its aqueous solution, although not particularly limited, is preferably about 0.05 to 1 W/V %. Sugars such as mannose, sugar alcohols such as mannitol, polysaccharides, etc. may be added suitably to the aqueous solution. Such additives serve as osmotic pressure adjusting agents and dispersants and act also to support the lipid vesicles when the resulting dispersion is subjected to freeze-drying or spray-drying as will be described later.

The mixing ratio between lipid vesicles and the dispersion medium, which is dependent on the kind of dispersion medium, is preferably 5 to 100 parts by weight of the latter per 1 part by weight of the former. The two ingredients are mixed together by a usual method which is suited to the kind of dispersion medium.

The drug-containing lipid vesicle preparation thus obtained is administered to man or animals usually orally, parenterally or externally, for example.

When the preparation obtained as above is liquid, the preparation can be optionally freeze-dried or spray-dried in the usual manner into a new solid preparation.

A conventional freeze-drying or spray-drying auxiliary agent may be added to the liquid preparation before freeze- or spray-drying. This makes the preparation easy to dry, gives improved stability to the resulting solid preparation and renders the preparation smoothly redispersible for use.

The solid preparation obtained in this way is redispersed in distilled water or the like before use and is administered to man or animals, for example, orally or parenterally.

The drug-containing lipid vesicle preparation of the present invention comprises lipid vesicles which are composed of an inner aqueous phase in the form of an aqueous solution or suspension and a membrane of phospholipid containing a lipophilic surfactant enclosing the aqueous phase therein, contains a drug in the inner aqueous phase and/or the membrane, and is in the form of a dispersion of the vesicles in a dispersion medium. Accordingly when the drug is contained in the inner liquid phase and the dispersion medium is liquid, the rate of dissolving-out of the drug is controllable by adjusting the difference in osmotic pressure between the inner liquid phase and the outer liquid phase. Furthermore, the size of vesicles or aggregations thereof is adjustable in accordance with the kind of dispersion medium, stirring condition for forming or dispersing the vesicles, dispersion concentration and other conditions, whereby the transferability of the drug to tissues or drug dissolving-out rate can be determined as desired. Thus, the present preparation has outstanding advantages. Moreover, the preparation can be higher than conventional liposome preparations in drug content and has higher stability than conventional multiple emulsions of the W/O/W type, hence very useful.

Drug-containing lipid vesicle preparations of the invention and the process for producing such preparations will be described with reference to the following examples.

EXAMPLE 1

A 350 mg quantity of FK-565 substance [1] was dissolved in 50 g of an aqueous solution containing 0.45% of sodium chloride and 5% of glucose. With stirring, the resulting solution ($W_1$) was added dropwise to a mixture (L) composed of 18 g of soybean lecithin, 9 g of sorbitan sesquioleate (SO-15) and 3 g of Panacete-810 [2], whereby $W_1/L$ was obtained wherein $W_1$ was enclosed with a membrane of L. A 2.85 g portion of $W_1/L$ was weighed out, to which was added an aqueous solution ($W_2$) containing 0.1% of Polysorbate-80 [3] and 5% of mannitol to obtain 100 g of a mixture. The mixture was stirred with use of a homomixer to effect dispersion, giving a preparation of lipid vesicles containing FK-565 substance ($W_1/L/W_2$). The content of FK-565 substance in the overall system was 0.1 mg/ml, and the aggregations of vesicles were about 100 μm in mean particle size. A release experiment was conducted with use of a diffusion cell to determine the release of FK-565 substance from $W_1$ into $W_2$ with time. Consequently sustained release was observed for 100 hours.

1) FK-565 substance:

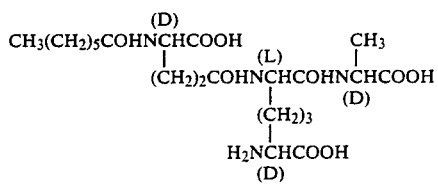

2) Panacete-810: trademark, product of Nippon Oils & Fats Co., Ltd.
3) Polysorbate-80: trademark, product of Nikko Chemicals Co., Ltd.

EXAMPLE 2

A 13.8 g quantity of sodium salt of ceftizoxime was dissolved in 46.2 g of distilled water for injection. With stirring, the solution ($W_1$) was added dropwise to a mixture (L) of 18 g of soybean lecithin, 18 g of sorbitan sesquioleate (SO-15) and 4 g of Panacete-810 to obtain an emulsion ($W_1/L$). To a 3.3 g portion of the emulsion weighed out was added dropwise the same amount of xylene, and the mixture was stirred to obtain a suspension. To the suspension was added 196.7 g of an aqueous solution ($W_2$) containing 0.1% of Polysorbate-80 and 5% of mannitol. The mixture was stirred (5000 r.p.m., 5 minutes) with use of a homomixer to effect dispersion, giving a preparation of lipid vesicles containing the sodium salt of ceftizoxime ($W_1/L/W_2$). The aggregations of vesicles were 1 to 10 μm in mean particle size.

One-gram portions of the dispersion were individually placed into vials cooled with liquid nitrogen, whereupon the dispersion was instantaneously frozen to a solid, with lipid vesicles enclosed in a mannitol cake. Each vial was dried in a vacuum at a temperature of up to −25° C. for 12 hours and then dried at 20° C. for 2 hours, affording a freeze-dried preparation of lipid vesicles containing 2 mg (potency) of ceftizoxime sodium salt. When the product was redispersed in water, the aggregations of vesicles were 2.1 to 5.6 μm in mean particle size.

The freeze-dried preparation obtained above was redispersed in 941 mg of distilled water for injection. The dispersion was administered to the tail vein of male mice (7-week-old, weighing 25 to 30 g) at a dose of 400 μg calculated as ceftizoxime sodium, and the concentration of the drug in blood was measured with lapse of time. Consequently a sustained concentration of 2 μg/ml was observed even 24 hours after the administration.

Of the redispersed preparation obtained in the same manner as above, a fraction of 5.6 μm in mean particle size was given to the tail vein of a male mice (7-week-old, weighing 25 to 30 g), which were then checked for the distribution of the drug through organs. In 30 minutes to 2 hours, the drug was found to have distributed chiefly through the lung, with a distribution also observed in the liver and the spleen.

When another fraction, 2.1 μm in mean particle size, was similarly given, the drug was found distributed mainly through the liver and the spleen, with a diminished distribution in the lung.

EXAMPLE 3

Insulin (8000 units) from the bovine pancreas was dissolved in 2087.5 mg of 0.1N hydrochloric acid. With stirring, the solution ($W_1$) was added dropwise to a mixture (L) of 720 mg of soybean lecithin, 720 mg of sorbitan sesquioleate and 160 mg of Panacete-810 to obtain a kneaded emulsion ($W_1/L$). The emulsion was added to 36 g of an aqueous solution containing 0.3% of Tween-80 and 8% of sorbitol, and the mixture was stirred (10000 r.p.m., 2 minutes), giving an insulin-containing lipid vesicle preparation, 70 μm in mean particle size.

The preparation was orally given (at a dose corresponding to 100 units of insulin) to male rats (6 week-old, weighing 180 to 200 g), and the blood was collected from the subclavian vein and checked for the blood sugar level with the lapse of time. Consequently the preparation produced a sustained effect to achieve about 40% blood sugar reduction over a period of 4 hours after the administration.

EXAMPLE 4

A 10 mg quantity of Ubiquinone-10 was dissolved in a mixture (L) of 720 mg of soybean lecithin, 180 mg of sorbitan sesquioleate and 100 mg of Panacete-810. A 9 g of physiological saline ($W_1$) was added dropwise to the solution with stirring to obtain a kneaded emulsion ($W_1/L$). To $W_1/L$ was added xylene in an amount 2 times the amount of the emulsion, whereby aggregations of $W_1/L$ were liberated, which were found to be 0.45 μm in mean particle size. The dispersion was added to 500 ml of an aqueous solution ($W_2$) containing 0.2% of polyoxyethylene (60) hardened castor oil and 5% of mannitol. The mixture was stirred for dispersion to obtain a lipid vesicle preparation.

EXAMPLE 5

Two ml of an aqueous solution ($W_1$) containing 10000 units of bovine pancreatic insulin was added dropwise to a mixture (L) of 720 mg of soybean lecithin, 180 mg of sorbitan sesquioleate and 100 mg of Panacete-810 with stirring to obtain a kneaded emulsion ($W_1/L$). $W_1/L$ was then added to an oily base comprising 180 mg of fluid paraffin, 220 mg of sorbitan sesquioleate, 2400 mg of white vaseline and 200 mg of white Japan wax, and mixed together by stirring to obtain an ointment of lipid vesicles containing insulin.

We claim:

1. A method for the preparation of a drug-containing lipid vesicle preparation comprising adding an aqueous solution or suspension to a phospholipid which contains a lipophilic surfactant to form a mixture, stirring said mixture whereby lipid vesicles are formed, then dispersing said vesicles in a dispersion medium to form an emulsion.

2. The method of claim 1 wherein said dispersion medium is an aqueous solution of at least one hyrophilic surfactant or is an oily base.

3. The method of claim 1 wherein said medium is an aqueous solution of at least one hydrophilic surfactant and said emulsion is a liquid further comprising freeze drying or spray drying said emulsion to form a solid preparation.

4. The method of claim 1 wherein said adding is carried out dropwise.

5. The preparation which is the product of the method of claim 1.

6. The preparation which is the product of the method of claim 2.

7. The preparation which is the product of the method of claim 3.

8. The preparation which is the product of the method of claim 4.

9. The preparation of claim 5 wherein said vesicles are dispersed in said aqueous solution of said hydrophilic surfactant and said emulsion has been freeze dried or spray dried to form a solid preparation.

10. A drug-containing lipid vesicle emulsion preparation comprising aggregations of lipid vesicles comprising
   a. an inner aqueous phase in the form of an aqueous solution or suspension containing a drug therein, and
   b. a membrane of phospholipid containing a lipophilic surfactant enclosing said aqueous phase, said vesicles dispersed in an aqueous solution of at least one hydrophilic surfactant or in an oily ointment base and constituting an emulsion.

* * * * *